United States Patent
Feiglin et al.

(10) Patent No.: US 8,936,708 B2
(45) Date of Patent: Jan. 20, 2015

(54) MANIPULATING THE SIZE OF LIQUID DROPLETS IN DIGITAL MICROFLUIDICS

(71) Applicant: Tecan Trading AG, Mannedorf (CH)

(72) Inventors: Marc N. Feiglin, East Brunswick, NJ (US); Michael Benjamin Franklin, Bailey, CO (US); Timothy Francis Lee, Forest Hill (AU); Joseph Mamone, Hillsborough, NJ (US)

(73) Assignee: Tecan Trading AG, Mannedorf (CH)

( * ) Notice: Subject to any disclaimer, the term of this patent is extended or adjusted under 35 U.S.C. 154(b) by 137 days.

(21) Appl. No.: 13/784,168

(22) Filed: Mar. 4, 2013

(65) Prior Publication Data
US 2013/0175169 A1 Jul. 11, 2013

Related U.S. Application Data

(63) Continuation-in-part of application No. 13/139,647, filed as application No. PCT/EP2009/067240 on Dec. 16, 2009.

(60) Provisional application No. 61/138,294, filed on Dec. 17, 2008.

(30) Foreign Application Priority Data

Dec. 17, 2008 (CH) ...................... 1979/08

(51) Int. Cl.
*G01N 27/447* (2006.01)
*G01N 27/453* (2006.01)
(Continued)

(52) U.S. Cl.
CPC ........ *G01N 27/447* (2013.01); *B01L 3/502715* (2013.01); *B01L 3/502792* (2013.01); *B01L 7/525* (2013.01); *B01F 13/0071* (2013.01);
(Continued)

(58) Field of Classification Search
USPC ................................................. 204/600, 450
See application file for complete search history.

(56) References Cited

U.S. PATENT DOCUMENTS

| 5,486,337 A | 1/1996 | Ohkawa |
|---|---|---|
| 6,565,727 B1 | 5/2003 | Shenderov |

(Continued)

FOREIGN PATENT DOCUMENTS

| EP | 1 094 120 | 4/2001 |
|---|---|---|
| EP | 1 143 252 | 10/2001 |

(Continued)

*Primary Examiner* — Alex Noguerola
(74) *Attorney, Agent, or Firm* — Notaro, Michalos & Zaccaria P.C.

(57) ABSTRACT

Liquid droplet manipulation instrument has electrode array for inducing movement of a droplet by electrowetting, substrate supporting the array and control with electrode selector connected to a voltage control. The selector selects each electrode and provides each with a controlled voltage. The control includes central processing unit for providing the selected electrode with an individual voltage pulse which is a drive voltage or a ground voltage or a stop voltage. The control defines a path for movement of a liquid portion of a larger volume that covers more than one electrode by the simultaneous selection of a group of two or more subsequent drive electrodes and to provide each selected drive electrode with a drive voltage pulse along the path. The control simultaneously provides a group of two or more electrodes adjacent to or identical with the pulsed drive electrodes, with a ground or stop voltage pulse.

21 Claims, 3 Drawing Sheets

(51) Int. Cl.
 *B01L 3/00* (2006.01)
 *B01L 7/00* (2006.01)
 *B01F 13/00* (2006.01)
 *C12Q 1/68* (2006.01)
 *B01L 3/02* (2006.01)

(52) U.S. Cl.
 CPC ............ *B01F 13/0076* (2013.01); *C12Q 1/686* (2013.01); *B01L 3/0268* (2013.01); *B01L 2200/027* (2013.01); *B01L 2200/0605* (2013.01); *B01L 2200/10* (2013.01); *B01L 2200/16* (2013.01); *B01L 2300/0819* (2013.01); *B01L 2300/1822* (2013.01); *B01L 2300/1883* (2013.01); *B01L 2400/0427* (2013.01)
 USPC ......................................... 204/450; 204/600

(56) References Cited

U.S. PATENT DOCUMENTS

| 6,911,132 B2 * | 6/2005 | Pamula et al. ................ 204/600 |
| 2007/0217956 A1 | 9/2007 | Pamula et al. |
| 2011/0220505 A1 | 9/2011 | Wang et al. |

FOREIGN PATENT DOCUMENTS

| EP | 1 666 149 | 6/2006 |
| WO | WO 2006/081558 | 8/2006 |
| WO | WO 2007/061943 | 5/2007 |
| WO | WO 2007/136386 | 11/2007 |
| WO | WO 2010/040227 | 4/2010 |
| WO | WO 2010/069977 | 6/2010 |
| WO | WO 2011/002957 | 1/2011 |
| WO | WO 2011/126892 | 10/2011 |

* cited by examiner

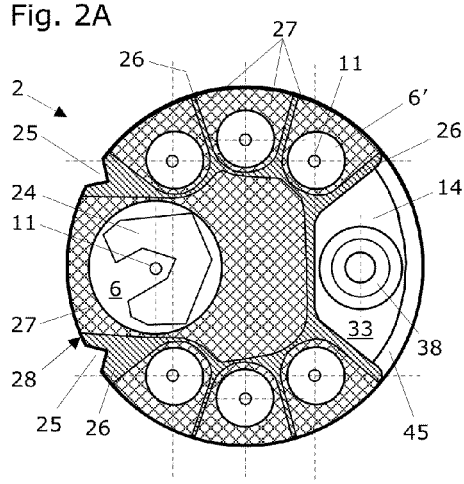
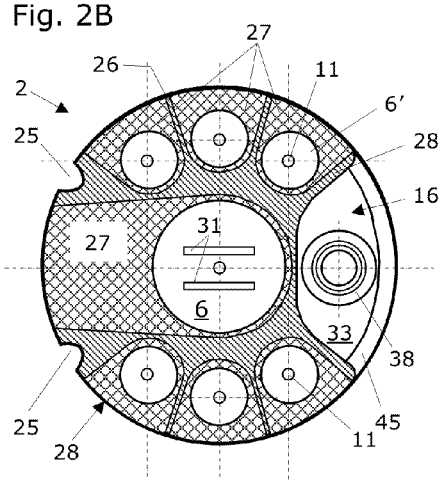
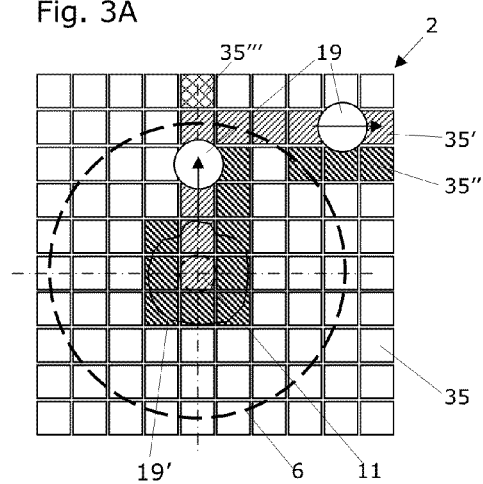
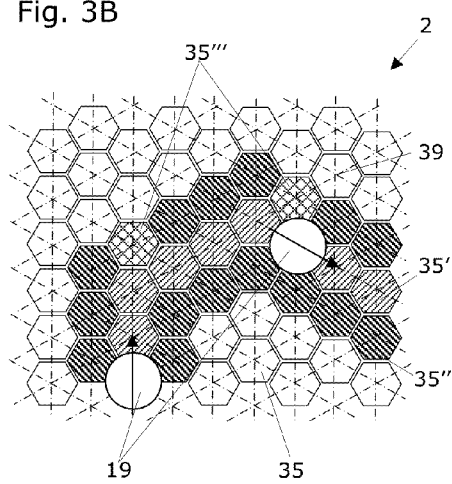
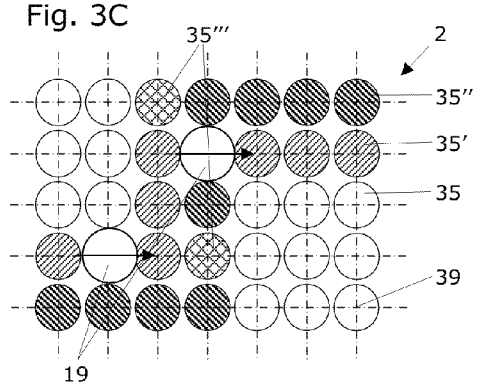
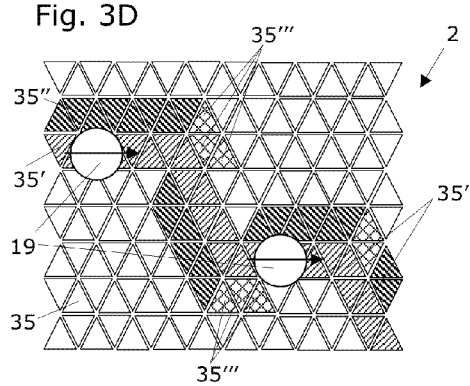

MANIPULATING THE SIZE OF LIQUID DROPLETS IN DIGITAL MICROFLUIDICS

RELATED PATENT APPLICATIONS

This is a Continuation In Part application of the U.S. patent application Ser. No. 13/139,647 published as US 2011/0290647 A1, which is the US national phase of the international application PCT/EP09/67240 filed on Dec. 16, 2009 that claims the priority of the U.S. provisional application 61/138,294 and of the Swiss patent application No. CH 01979/08, both filed on Dec. 17, 2008; the entire disclosure of all these applications is herein incorporated by explicit reference.

FIELD OF TECHNOLOGY

The present invention relates to manipulating the size of liquid droplets in digital microfluidics. This technical field generally relates to the control and manipulation of liquids in a small volume, usually in the micro- or nanoscale format. Movement of small liquid volumes in a channel system is known per se as, e.g. being controlled by micro pumps in stationary devices or centripetal forces in rotating labware. In digital microfluidics however, a defined voltage is applied to electrodes of an electrode array, so that individual droplets are addressed by electrowetting. For a general overview of the electrowetting method, please see Washizu, IEEE Transactions on Industry Applications, Volume 34, No. 4, 1998, and Pollack et al., Lab chip, 2002, Volume 2, 96-101. Briefly, electrowetting refers to a method to move liquid droplets using arrays of microelectrodes, preferably covered by a dielectric layer that comprises a hydrophobic surface. By applying a defined voltage to selected electrodes of the electrode array, a change of the surface tension of the liquid droplet, which is present on the hydrophobic surface above the addressed electrodes, is induced. This results in a remarkable change of the contact angle of the droplet on the addressed electrode, hence in a lateral movement of the droplet. For such electrowetting procedures, two principle ways to arrange the electrodes are known: using one single surface with an electrode array for inducing the movement of droplets or adding a second surface that is opposite a similar electrode array and that provides at lest one ground electrode. A major advantage of the electrowetting technology is that only a small volume of liquid is required, e.g. a single droplet. Thus, liquid processing can be carried out within considerably shorter time. Furthermore the control of the liquid movement can be completely under electronic control resulting in automated processing of samples.

RELATED PRIOR ART

A device for liquid droplet manipulation by electrowetting using one single surface with an electrode array (a monoplanar arrangement of electrodes) is known from the U.S. Pat. No. 5,486,337. All electrodes are placed on a surface of a carrier substrate, lowered into the substrate, or covered by a non-wettable surface. A voltage source is connected to the electrodes. The droplet is moved by applying a voltage to subsequent electrodes, thus guiding the movement of the liquid droplet above the electrodes according to the sequence of voltage application to the electrodes. Dispensing of a droplet is disclosed by an electrostatic pipette that consists of a non-wettable tube adjacent to a tubular wettable primary electrode exposed to a source of sample liquid. Annular, non-wettable secondary electrodes are spaced axially along the non-wettable tube from the primary electrode, into which the sample liquid enters by capillary action. Voltage is sequentially applied between primary electrode and secondary electrodes along the non-wettable tube. Consequently, a portion of the sample liquid is electrostatically charged by the primary electrode and then attracted in the form of a charged droplet by the consecutive secondary electrodes.

An apparatus with a single-sided electrode design for manipulating droplets is also known from U.S. Pat. No. 6,911,132 B2, all conductive elements being contained on a first surface on which droplets are manipulated. An additional surface can be provided parallel with the first surface for the purpose of containing the droplets to be manipulated. The apparatus enables droplet manipulating such as merging and mixing two droplets together, splitting a droplet into two or more droplets, sampling a continuous liquid flow by forming from the flow individually controlled droplets, and iterative binary or digital mixing of droplets to obtain a desired mixing ratio. Merging is performed using at least three aligned drive electrodes that initially are switched off, the first and third electrode each bearing a drop of liquid on top of the surface covering it. Consecutively, all three electrodes are activated thereby drawing the two droplets towards each other across the second (central) electrode until they form a single meniscus that joins the two droplets. Then, the two outer electrodes are returned to the ground state and the merger drop is concentrated on the central electrode that is still activated. In order to split the merger drop again, all three electrodes are grounded before all three electrodes are activated thereby drawing the merger drop laterally outwardly and spreading it on the three electrodes. Consequently, a shrinking meniscus forms over the central electrode and by activating both outer electrodes, the merger drop eventually breaks into two essentially equal droplets that are positioned on the first and third electrode. Merging droplets is also disclosed by Washizu 1998. Merging and splitting of droplets is also disclosed by Pollack et al. 2002.

An electrowetting device for microscale control of liquid droplet movements, using and electrode array with an opposing surface with at least one ground electrode of is known from U.S. Pat. No. 6,565,727 (a biplanar arrangement of electrodes). Each surface of this device may comprise a plurality of electrodes. The drive electrodes of the electrode array are preferably arranged in an interdigitated relationship (see also U.S. Pat. No. 6,911,132 B2) with each other by projections located at the edges of each single electrode. The two opposing arrays form a gap. The surfaces of the electrode arrays directed towards the gap are preferably covered by an electrically insulating, hydrophobic layer. The liquid droplet is positioned in the gap and moved within a non-polar filler fluid by consecutively applying a plurality of electric fields to a plurality of electrodes positioned on the opposite sites of the gap. A drop meter with larger area defined by a hydrophobic surface of a control pad is connected via a small extension to a path or driveway of drive electrodes, the first one being a cut-off electrode and the second one being a control electrode. A wetting potential is first applied to the cutoff electrode, the liquid which has covered the surface of the control pad thus spreading over the cutoff and drive electrodes. Consequently, the wetting potential is removed from the cutoff electrode, making it hydrophobic again. Part of the liquid moves back to the contact pad ad is replaced by the non-polar filler fluid. As a result, an isolated drop of liquid is separated and formed on the control electrode.

The use of such an electrowetting device for manipulating liquid droplets in the context of the processing of biological samples is known from the US patent application No. 2007/

0217956 A1. Here it is suggested to amplify nucleic acids on a printed circuit board for example through thermocycling. The droplets are transported on an array of electrodes by applying a potential between a reference electrode and one or more drive electrodes. The sample is placed into a reservoir on the printed circuit board, and droplets are dispensed on said printed circuit board.

A container with a polymer film for manipulating samples in liquid droplets thereon is known from WO 2010/069977 A1. The polymer film is placed onto a liquid droplet manipulation instrument that comprises an electrode array and is kept at a distance to a base side of the container thus creating a gap where the manipulation of samples in liquid droplets takes place. Separation of a liquid droplet from a liquid portion that covers several electrodes is performed by drive voltage pulses applied to subsequent drive electrodes leading away a separated liquid droplet from the liquid portion.

From WO 2010/040227 A1 is known a hybrid digital and channel microfluidic device in the form of an integrated structure in which a liquid droplet may be transported by a digital microfluidics array and transferred to a microfluidic channel. Merging two liquid separate droplets by moving them on two separated driveway and then joining these electrode paths is also disclosed.

An electrode configuration for dispensing of liquid droplets by the use of a dielectric layer placed on the electrode array that features portions with different dielectric constants is disclosed in WO 2011/002957 A2. It is noted there that with respect to droplet operations in digital microfluidics, the higher the dielectric constant (k) at a certain electrode, the lower the required electrowetting voltage for performing droplet operations, and conversely, the lower the dielectric constant (k) at a certain electrode, the higher the required electrowetting voltage for performing droplet operations. According to this basic principle, a "higher" voltage is applied to a reservoir electrode and a dispensing electrode for wetting both electrodes with a sample liquid. Reducing the voltage to a "lower" value in an area between the reservoir electrode and the dispensing electrode will separate a portion of the liquid on the dispensing electrode. Because the dielectric constant is inversely proportional to the thickness of the chosen material, varying the thickness of dielectric layer regions may be used for defining portions with different dielectric constants. Combining low-k and high-k dielectric segments of equal thickness is also disclosed. In addition, structural obstacles that require "higher" voltages and combinations with low-k and high-k dielectric regions are disclosed as well.

OBJECTS AND SUMMARY OF THE PRESENT INVENTION

It is a first object of the present invention to suggest an alternative device which enables a simplified manipulation of liquid droplets in a microscale format. This object is achieved according to a first aspect by a liquid droplet manipulation instrument as herein described and disclosed.

It is second object of the present invention to suggest a device which enables the fully integrated handling of biological samples in a simple, automated and rapid manner, starting the handling with the provision of a sample to be analyzed for its biological material into the device and finalizing the processing with the achievement of a final analysis. This object is achieved according to a second aspect by a biological sample processing system as herein described and disclosed.

It is third object of the present invention to suggest an alternative method for processing a biological sample using a digital microfluidics sample processing system. This object is achieved according to a third aspect by a method for processing a biological sample using the biological sample processing system as herein described and disclosed.

Additional preferred features according to the present invention result from the dependent claims.

Advantages of the present invention comprise:

The system provides a multi-component device adjusted for a fully automated processing of biological samples up to the analysis.

Such a fully integrated system that can directly accept macro-volumes of sample (either in liquid form or on a solid surface such as a buccal swab) and process utilizing nano-volumes; all without any user interaction.

The distinction between disposable and non-disposable components allows the automated processing in a standardized and cost-efficient manner.

A feature of this invention is that small aliquots of reagents can be manipulated from a larger starting volume. This allows large, arbitrary amounts of fluid to be introduced to the cartridge (by a user or an instrument) without a requirement for high precision. This further allows the device to be used by a larger range of users, including ones that cannot add precise volumes and/or to be made less expensively.

BRIEF DESCRIPTION OF THE DRAWINGS

The present invention will be explained in more detail on the basis of exemplary embodiments and schematic drawings. These explanations however should not restrict the scope of the present invention. Furthermore, the relative dimensions shown in the figures may vary considerably, as these schemes are not drawn to scale. There is shown in:

FIG. 2 a top view on a container and a film of a biological sample processing system according to the present invention, wherein:

FIG. 2A shows the at least one well for positioning the biological sample being arranged towards the outer margin of the container, and FIG. 2B shows the at least one well for positioning the biological sample being arranged in the center of the container;

FIG. 3 top views of different embodiments of preferred electrode arrays, wherein in:

FIG. 3A each electrode is accomplished in form of a rectangle;

FIG. 3B each electrode is accomplished in form of a hexagon;

FIG. 3C each electrode is accomplished in form of a circle; and

FIG. 3D each electrode is accomplished in form of a triangle.

FIG. 4 top views of a grid-like electrode array according to a first preferred embodiment and similar to the array of FIG. 3A with rectangular electrodes, wherein in:

FIG. 5 top views of a grid-like electrode array according to a second preferred embodiment and similar to the array of FIG. 3A with rectangular electrodes, wherein in:

FIG. 6 top views of a grid-like electrode array according to a third preferred embodiment and similar to the array of FIG. 3A with rectangular electrodes and an electrode path adjacent to the array, wherein in:

DETAILED DESCRIPTION OF THE INVENTION

Figure 1:
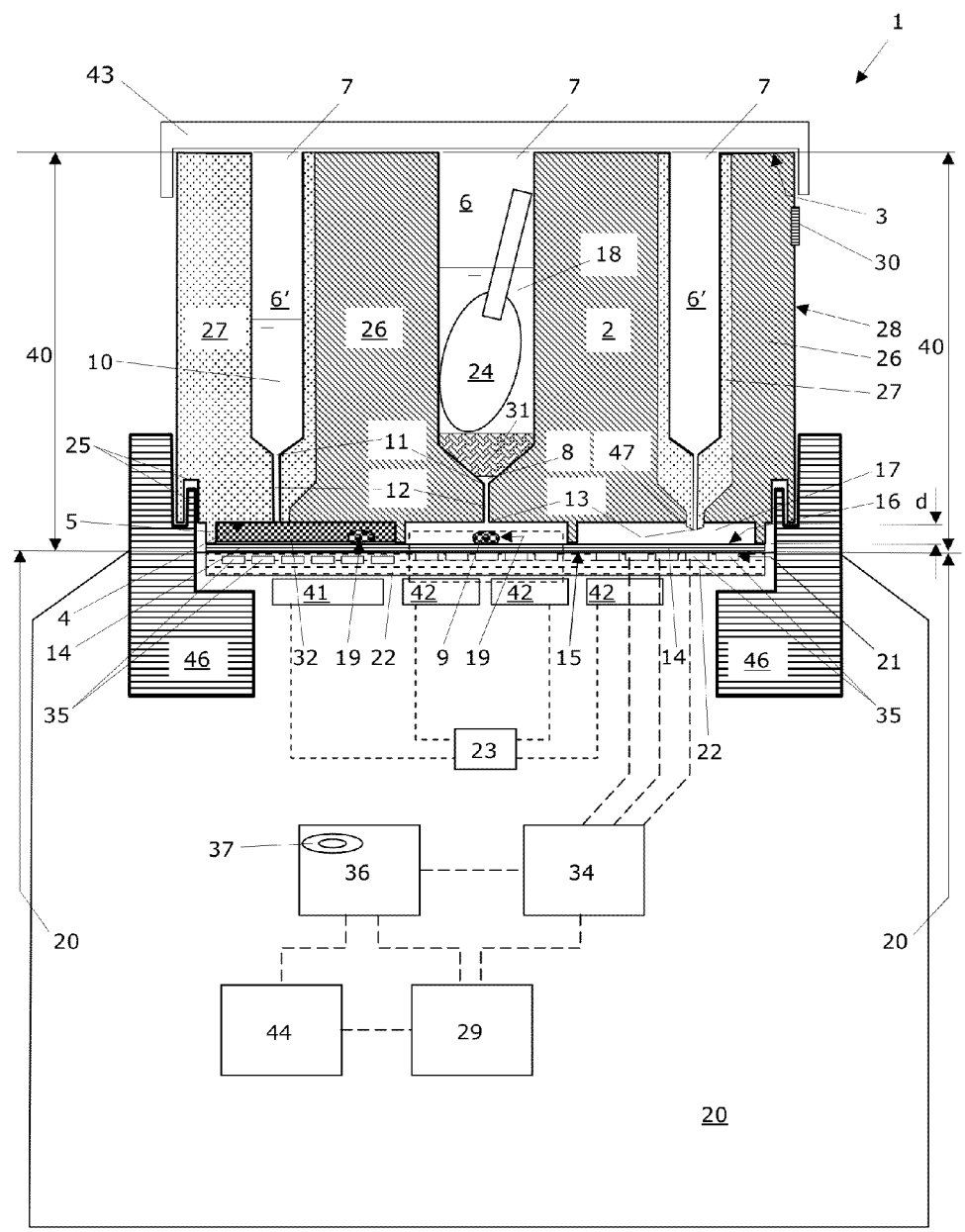
FIG. 1 a schematic cross section and partial layout of a biological sample processing system according to the first aspect of the present invention.

FIG. 1 shows a schematic cross section and partial layout of an exemplified biological sample processing system 1 according to the first aspect of the present invention. For enabling the processing of biological samples in an automated and cost-efficient manner, this system 1 comprises distinct single components which can be assembled to one unit, the system 1, in simple steps. Such component is for example a container 2 which is comprised by the biological sample processing system 1. The container 2 is accomplished for processing large volumes of liquid 18. In the context of the present invention, large volumes of liquid are understood to relate to liquid volumes up to 5 ml or up to 10 ml, depending on the sample to be hosted. For example, in case a buccal swab is used, the large volume well is preferably designed to hold volumes up to 2 ml; if holding for example whole blood, the well preferably holds up to 5 ml. The container 2 has a top side 3 and a base side 4. At its base side 4, the container 2 comprises protrusions 5. These protrusions 5 may be accomplished as parts of the container 2 extending downwardly at the base side 4. Alternatively these protrusions 5 may be attached to the base side 4 of the container 2 separately, for example by gluing, welding or other appropriate means to stably attach such protrusions 5 to the base side 4 of the container 2. The container 2 comprises at least one well 6. This at least one well 6 is open at its top side 7. Thus, a biological sample 9, a reaction reagent 10, or both can be positioned within this well 6. At its bottom side 8, the at least one well 6 has at least one opening 11. This opening is connected by a channel 12 of the container 2 with an orifice 13 of the container 2 at its base side 4. In the case a liquid 18 or a liquid droplet 19 is placed into the at least one well 6 (with or without a reaction reagent, and/or with or without at least parts of the biological sample 9), it can be transferred out of the well 6 through the channel 12. The diameter of the channel 12 preferably is chosen such that the capillary force prevents liquid from leaking out the orifice 13 and that the liquids thus stay inside the at least one well 6 without need for a valve or any other closure of the channel 12. The diameter of the channel 12 preferably is from 100 μm to 1 mm.

Furthermore the biological sample processing system 1 comprises a flat polymer film 14. This flat polymer film 14 could also be called a "plastic skin" as proposed by Yang et al. (2008) "Exchangeable, pre-loaded "Skin Depot" for digital microfluidics" at the MicroTAS meeting in San Diego, Calif. This flat polymer film 14 preferably has a lower surface 15 and a hydrophobic upper surface 16. As a material for the thin polymer films, food wraps, and stretchable wax films can be used. When assembling the single components to the biological sample processing system 1 in a first step by positioning the container 2 on the film 14, the hydrophobic upper surface 16 of the film 14 is abutted by the protrusions 5 of the container 2. Thereby, the protrusions 5 keep the flat polymer film 6 at a distance "d" to the base side 4 of the container 2. This distance "d" is set by the height of the protrusions 5 of the container 2, and defines at least one gap 17 when the container 2 is positioned on the flat polymer film 14. The gap 17 between the upper hydrophobic surface 16 of the film 14 and the base side 4 of the container is sized to accommodate a liquid droplet. Preferably, this gap 17 is less than 2 mm. Most preferably, the gap 17 is less than 1 mm.

The biological sample 9 preferably is contained a well 6. It can be mixed with a liquid 18, such as a buffer solution with or without lysis reagents. The biological sample 9 may be displaced from the at least one well 6 (while kept within a liquid droplet 19), through the channel 12 of the container 2 onto the hydrophobic upper surface 16 of the flat polymer film 14. The liquid droplet 19 with the biological sample 9 is thus placed in the gap 17 between the film 14 and the container 2.

The displacement may be performed, without using valves, by a pressure applied, centrifugal force, or electrowetting against the capillary forces that prevent leaking of liquids out of the wells 6,6'. However, also other means may be used which are suitable to displace the liquid 18 or liquid droplet 19 from the well 6 onto the hydrophobic upper surface 16 of the flat film 14. These means for displacement may also be used for transferring a reaction reagent 10, which is stored in a well 6' of the container 2, onto the upper surface of the film. When displacing liquids from the wells 6,6' onto the upper polymer film surface 16, excess air form the gap may be vented e.g. via an empty well 6'.

For the manipulation of liquid droplets 19, which had been preferably displaced from the at least one well 6 of the container 2 onto the upper surface 16 of the film 14, the biological sample processing system 1 comprises furthermore a liquid droplet manipulation instrument 20. This instrument 20 comprises at least one electrode array 21, a substrate 22 which supports the at least one electrode array 21 and a control unit 23. The liquid droplet manipulation instrument 20 is accomplished so that the container 2 and the film 14 can be reversibly attached to the instrument 20. Thereby, the lower surface 15 of the film 14 abuts the electrode array 21. When assembled in this a way, the biological sample processing system 1 enables the displacement of a liquid droplet 19 from the at least one well 6 of the container 2 onto the upper surface 16 of the flat polymer film 14 and accordingly above the at least one electrode array 21. The electrode array 21 is accomplished to induce movements of the liquid droplets 19. Thus, the instrument 20 is accomplished to control a guided movement of said liquid droplet 19 on the upper surface 16 of the flat polymer film 14 by electrowetting and to process there the biological sample 9.

Typical biological samples 9 which are processable by a biological sample processing system 1 are nucleic acids or proteins. Preferably, nucleic acids are used for processing. Such nucleic acids comprise DNA (desoxyribonucleic acid, for example genomic DNA, cDNA, mtDNA), RNA (ribonucleic acid, for example mRNA), being single- or double stranded, and derivatives thereof (for example artificially labeled nucleic acids. These biological samples 9 may be contained in tissue samples such as oral mucosa cells or hair follicles. Likewise the biological samples 9 may be contained in a liquid, such as samples of body fluids such as blood, urine, sputum etc. A biological sample 9 of interest can be processed by a biological sample processing system 1 according to the present invention independent of its origin. Of particular interest are samples taken for example from patients (in routine diagnostic procedures) or from a crime scene (in criminal forensics). However, for a successful processing of the sample, the selection of required reaction reagents 10 should be adopted based on the material which comprises the biological sample 9. It is also possible to load an already purified biological sample 9 into the at least one well 6 of the container 2. In this case, a purification step is not necessarily required during the processing within the biological sample processing system 1.

Preferably, the at least one well 6 of the container 2 is sized to accommodate a solid substrate 24 which carries the biological sample 9. This solid substrate 24 might be a tissue sample. However, it is also possible that this solid substrate 24 is a swab, a spatula, a needle, a syringe, a piece of paper such as FTA paper, or fabric material such as clothing, or other substrate suitable for carrying and/or collecting a biological sample 9 or e.g. tissues comprising the sample 9. Most preferably, the solid substrate 24 is a swab head, and accordingly, the at least one well 6 of the container 2 is sized to accommodate a swab head. An exemplary embodiment of a well 6 accommodating a swab head is shown in FIG. 1. A typical size of such a well 6 for a swab head has a diameter of about 10 mm and a height of about 40 mm. Such a swab head may be made for example of cotton or polyester, as commonly known in the art. These solid samples 24 may carry as well tissue samples or biological samples 9 in form of a liquid (such as bodily fluids).

In the present FIG. 1, a container 2 is shown to comprise one well 6 sized to accommodate a swab head, and further wells 6' which are different from the sample well 6 in size. In another variant, as shown in FIGS. 2A and 2B, the container 2 comprises at least one sample well 6 and six smaller wells 6' for storing reaction reagents. These wells 6' are preferably sized to store reaction reagents 10 and other required liquid such as buffers. A typical size of such a well 6' for storing reaction reagents 10 has a diameter of about 5 mm and a height of about 40 mm. However, the size of each well 6,6' of the container 2 may be adopted individually according to the requirements given by the underlying question to be solved.

Similarly, the position of the wells 6,6' within the container 2 may be adopted as depending on the design of the liquid droplet manipulation instrument 20, production methods etc. Preferably the wells 6,6' are positioned in the outer regions of the container 2, to provide a central area beneath the container for moving liquid droplets 19 and for processing the sample 9 within the liquid droplet 19. For processing, drops of reaction reagents 10 can be transferred onto the hydrophobic upper surface 16 of the flat polymer film 14 and mixed there with a droplet 19.

The at least one well 6 having a solid substrate 24 carrying the biological sample 9 may also comprise a reaction reagent 10. Preferably, such a reaction reagent 10 is suited to free the biological sample 9 from the material it is contained in. A lysis reagent for example would be well suited for these purposes. It might comprise a reaction buffer and means to enzymatically open the cellular envelope hosting the biological sample 9. The reaction reagent 10 may be positioned within the well 6 in form of a liquid. Depending on the application and availability however, the reaction reagent 10 may alternatively be positioned within the well 6 for example in a lyophilized form. This form of reaction reagent 10 is preferred in the case when the container should be purchasable having preloaded reaction reagents 10. However it is the general knowledge of a skilled person that the lyophilized form of a reaction reagent is only preferred when the lyophilization process has no or only minor influences on the functionality of the reagent 10.

In a preferred embodiment, the container 2 of the biological sample processing system 1 comprises at least one well 6 which is accomplished as storage for a reaction reagent 10. This embodiment is particularly preferred in case the container 2 comprises already one well 6 for positioning a biological sample 9. Thus, in this situation, the container comprises at least two wells 6, one well 6 for positioning the biological sample 9 and one well 6' for storing a reaction reagent. Stored reagents 10 comprise reagents selected from a group comprising reagents for performing cell lysis, reagents for performing nucleic acid purification, reagents for performing nucleic amplification and reagents for performing sequencing of nucleic acids.

During cell lysis, the cellular integrity is disrupted by opening cell membranes. This step can be performed using for example enzymatic activity or chemical lysis. However other procedures to disrupt cellular integrity may be suitable. Exemplarily, the thermostable protease EA1 manufactured by ZyGem™ Corporation (Waikato Innovation Park, Ruakura Road, Hamilton, New Zealand) should be mentioned at this place as a suitable enzyme for performing cell lysis. Alternatively, cell lysis may be carried out using Proteinase K, or chemical lysis, both procedures also well known in the art. The buffer matching to the used enzyme can be chosen by a skilled person without the need of special efforts and is regarded to be based on the general knowledge in the art, too. As the procedure of performing cell lysis is well known to a skilled person, it should not be described here in more detail.

DNA purification processes are well known in the art, too, and the single procedural steps should not be explained here. A purification step is preferred in such cases where the sample mixture comprises elements which might distract following reactions. In the context of this application, such a purification step is desired preferably after a cell lysis or after nucleic acid amplification processes such as polymerase chain reaction or sequencing by synthesis. Preferably, DNA is to be purified. Typically, reagents for performing nucleic acid purification comprise beads or particles, eventually modified, which are capable to bind DNA directly or indirectly. After DNA-binding, undesired contents of the sample mixture can be washed off, and DNA can be resolved in a desired liquid. Such beads may be standard magnetic beads well known in the art. Advantageous beads include DNA IQ™ offered from Promega Corporation (2800 Woods Hollow Road, Madison, Wis. 53711 USA) or Dynal® Magnetic Beads offered from Invitrogen Ltd (European Headquarters: 3 Fountain Drive, Inchinnan Business Park, Paisley PA4 9RF, UK). Suitable beads or particle may also be modified. Such a modification may simplify and specify the purification, as is mediates binding of specifically labeled DNA. DNA labeling can be achieved during an amplification process. A typical label used for primer in polymerase chain reaction is biotin; however, other labels suitable can be used in the context of the present invention. The labeled primer, incorporated into the amplicon, can be captured in the subsequent purification process using for example streptavidin coated beads. However, other systems suitable for the purification of amplified DNA may be used. For example Dynal® Magnetic beads may be used also in this second purification step.

Polymerase chain reaction (PCR) is typically used for the amplification of nucleic acid and is also well known in the art. Shortly, PCR comprises a cyclic repetition of three basic, temperature specific steps: a nucleic acid denaturation step separating the double strands of DNA at preferably 98° C., an annealing steps allowing preselected primer (oligonucleotides) to bind to respective sequences on the single strand, wherein this temperature step depends on the primer sequence, and an extension step involving a polymerase which extends bound primer to a nucleic acid strand at an enzyme specific temperature. The polymerase is preferably thermostable, so that it is not influenced by the denaturation temperature. Such a thermostable polymerase well known in the art is the polymerase of the bacterium *Thermus aquaticus* (Taq-polymerase). However, other thermostable polymerases available may be used. Preferred templates are genomic DNA or cDNA. Using PCR, pre-selected, specific regions of a template may be amplified, giving for example more information about the origin of the DNA. Preferred regions to be analyzed by PCR comprise mitochondrial DNA (mtDNA), typical short tandem repeats (STR), or distinct single nucleotide polymorphisms (SNPs) known for being for example linked with specific diseases (used as genetic markers).

Sequencing of specifically amplified DNA is a well known tool to further characterize the selected DNA. Major sequencing principles are known in the art, sequencing by amplification and sequencing by hybridization. Sequencing by amplification involves a PCR-related process using however labeled stop-primer which terminate the extension process randomly. The resulting end-labeled fragments are then used for determining the sequence of the template. Sequencing by hybridization (SBH) involves the linkage of labeled primer to a matrix. Primer are selected so that the overlap partially in their sequence. After hybridization of a target DNA to said primer, sequence can be determined by the analysis of primer sequenced to which the target is bound. When applying sequencing by hybridization step with the biological sample processing system 1, the labeled primers are preferably linked to the hydrophobic upper surface 16 of the flat polymer film 14 prior to the start of sample processing. Most preferably, the labeled primers are linked prior to the release of the system into the trade.

In the case, two ore more, preferably all methods presented above should be performed using the biological sample processing system 1 according to the resent invention, it is required that the container 2 comprises more than two wells 6,6'. Preferably, the container 2 comprises at least one well 6 for positioning a biological sample 9 and further wells 6' for storing the required reaction reagents 10, with one dedicated well 6' for each reaction reagent 10 of one method. Preferably, the well 6 for positioning the biological sample 9 is accomplished to store additionally reaction reagents 10 and buffers required for cell lysis. Cell lysis can thus be performed directly in the well 6 which holds the biological sample 9.

Should all methods mentioned above be performed, the container 2 then comprises at least four wells 6,6': one well 6 for positioning the biological sample 9 and storing reaction reactions 10 for cell lysis, one well 6' for storing reaction reagents 10 for DNA purification, one well 6' for storing reaction reagents for PCR, and one well 6' for storing reaction reagents 10 for sequencing. Most preferably, the container 2 comprises at least ten wells 6,6' for processing of a biological sample 9:

at least one well 6 is accomplished for positioning the biological sample 9, for storing reaction reagents 10 and buffer and for performing cell lysis, at least three wells 6' are accomplished for pre-PCR purification (one each for magnetic beads, wash buffer, and elute buffer), at least two wells 6' are accomplished for amplification (one for storing the enzyme and buffer, one for storing the primer, with one primer well per locus to be amplified), at least two wells 6' are accomplished for post-PCR cleanup (one for storing streptavidin coated beads and one for storing wash buffer), at least two wells 6' are accomplished for storing reaction reagents 10 and buffer for sequencing by hybridization (one for storing buffer comprising a reference probe and one for storing buffer comprising a probe of interest).

Generally, the number of wells 6,6' is dependent on the type of reaction system used (required reagents, processing steps) and the number of analysis required (number of sequences/loci to be analyzed, i.e. STR, SNP, mtDNA) and may be adopted by a skilled person based on general knowledge in the art. If the primer for the amplification should be stored in the container 2, preferably the container 2 comprises one primer well per loci to be analyzed for the amplification process. Thus, in case 16 loci should be analyzed, the container preferably comprises 16 primer wells 6' for the amplification. In another preferred variant, the primer required for the amplification step may be available in dried form on the hydrophobic upper surface 16 of the flat polymer film 14, so that for storing primer, no separate well 6' would be required here in the container 2. The primer may in this case be re-suspended on the film 14 using a buffer held in a well 6'. For the sequencing by hybridization step, the number of wells 6' required storing reaction reagents 10 and buffer may similarly be adopted.

In an especially preferred embodiment, the biological sample processing system 1 is accomplished to perform the extraction, purification, amplification and analysis of a biological sample 9 of interest. Thus, the present invention provides according to the first aspect a fully integrated system that can directly accept macro-volumes of sample (either in liquid form or on a solid surface such as a buccal swab) and process utilizing nano-volumes up to the final analysis.

In the FIGS. 2A and 2B, a container 2 according to the present invention is shown in a top view, having one well 6 for positioning the biological sample 9 and six further wells 6' for storing reaction reagents 10.

When cell lysis is performed directly within the well 6 for positioning the biological sample 9, the biological sample 9 is set free from the cellular context, and preferably released into a liquid 18, which therefore is a reaction solution resulting from the cell lysis. In case the biological sample 9 was not contained in one or more cells when positioned into the well 6 of the container 2 (if lysis is not required), the liquid can be chosen according to the following procedural steps, and added into the well via the top side 7 of the well 6. In each case, the biological sample 9 should be contained at least in parts in a liquid for the further processing using the biological sample processing system 1 according to the first aspect of the present invention. The liquid 18 or a liquid droplet containing at least parts of the biological sample 9 is then displaced for further processing from the well 6 through the channel 12 of the container 2 onto the hydrophobic upper surface 16 of the flat polymer film 14.

The displacement preferably performed, without using valves or other moveable means, by a pressure applied, by centrifugal force, or by electrowetting. All these preferred displacement means act against the capillary forces that prevent leaking of liquids out of the wells 6,6'. However, also other means may be used which are suitable to displace the liquid 18 or liquid droplet 19 from the well 6 onto the hydrophobic upper surface 16 of the flat film 14.

As for further processing, the container 2 and the flat polymer film 14 are reversibly attached to the liquid droplet manipulation instrument 20, with the lower surface 15 of the film 14 abutting the electrode array 21. Accordingly, the liquid droplet 19 is displaced from the well 6 above the electrode array 21. In this arrangement, the liquid droplet 19 may be moved in a guided manner by the liquid manipulation instrument 20 by electrowetting. The movement is controlled to achieve the selected processing of the biological sample 9 contained within said liquid droplet 19 and to carry out this processing at preferred sites of the electrode array.

In a variant of the biological sample processing system 1, the liquid droplet 19 is moved in the gap 17 within an immiscible system liquid 32. This variant is the preferred embodiment, when performing PCR on the biological sample 9 contained in the at least one liquid droplet 19. As PCR requires the exposure of such a liquid droplet 19 to different temperatures, including the denaturation step at about 98° C., evaporation of liquid may be prevented or at least considerably reduced with the use of such an immiscible system liquid 32. Preferred system liquids immiscible with the liquid droplet 19 are selected e.g. from silicon oil, hexadecane and benzene.

For a form-fitted attachment of the container 2 to the liquid droplet manipulation instrument 20, both, container 2 and instrument 20 preferably comprise each at least one positioning element 25. Such positioning elements are preferably selected from a group comprising:

- at least one groove in the lateral area 28 of the container 2 and at least one elevation extending from the instrument 20 in such a way that when the container 2 with the film 14 is attached to the instrument 20, groove and elevation are arranged form-fitting to each other;
- at least one groove on the base side 4 of the container 2 and at least one elevation extending from the instrument 20 in such a way that when the container 2 with the film 14 are attached to the instrument 20, groove and elevation are arranged form-fitting to each other;
- at least one groove on the base side 4 of the container 2 and at least one elevation extending from the instrument 20 in such a way that when the container 2 with the film 14 are attached to the instrument 20, groove and elevation are arranged form-fitting to each other, wherein the at least one elevation extending form the instrument 20 is a Peltier element for locally providing the container 2 with a preselected temperature; and
- the container 2 having an irregular polyhedron shape and the liquid manipulation instrument having a corresponding groove, so that when attaching the container 2 to the instrument 20, both are aligned in a form-fitted snugly manner.

Positioning elements 25 accomplished as at least one groove of the container 2 and at least one elevation extending from the instrument 20 are presented in FIG. 1 (with the groove at the base side 4 of the container 2), FIG. 2A (with two triangular-shaped grooves in the lateral area of the container) and in FIG. 2B (with two semi-circular shaped grooves in the lateral area of the container 2). When using a Peltier element for heating the well 6 for positioning the biological sample 9, such Peltier element can be accomplished as an elevation extending from the instrument 20, its position may be chosen so that for example, is specifically provides the well 6 (whether this is central or not) with a defined temperature. However, other means for positioning the container 2 on the liquid droplet manipulation instrument 20 in a defined configuration may as well be used which are well known to a skilled person, and should not be described in more detail here.

While the container 2 is positioned on the liquid droplet manipulation instrument 20, a liquid droplet 19 on the flat polymer film 14 may either contact only the hydrophobic upper surface 16 of the film 14 or may contact both, the hydrophobic upper surface 16 of the film 14 and the base side 4 of the container 2. The contact surfaces of such a liquid droplet 19 may be influenced by the sizing of the gap 17 (thus, sizing the protrusions 5) or by sizing the liquid droplet 19.

The container 2 is preferably made by injection molding. In this way, the production costs may be reduced despite the achievable high manufacturing quality and the container 2 can be utilized as a low cost disposable. Such a single-serving container 2 is suited to be sold for various applications and can be equipped with a specific set of reaction reagents 10. The container 2 is preferably made either of an electrically insulating material 26, of an electrically conductive material 27, or of a combination of both an electrically conductive and an electrically insulating material 26,27. When made of two different materials, a two step injection process is preferred. In the FIGS. 1, 2A, and 2B, the core of the container 2 is made of an electrically insulating material 26, wherein the regions surrounding the wells 6,6' are made from an electrically conductive material 27. The surrounding regions made of the conductive material 27 are separated from each other by the insulating material 26. These surrounding regions made of conductive material 27 may form at the base side 4 of the container 2 a nozzle 47, which slightly extends into the gap 17 (see FIG. 1). The advantage provided by such a nozzle is the possibility to distinctly produce and deliver a liquid droplet 19 into the gap without the droplet 19 contacting the surface of the base side 4 of the container 2. Furthermore such a nozzle may enable a directed delivery of the droplet 19 into the gap 17.

Furthermore, parts of the surrounding regions made from the electrically conductive material 27 form a part of the outer, lateral side 28 of the container 2. Such a variant has the advantage, that each electrically conductive region 27 of the container 2 may be individually contacted electrically. This allows the conductive regions to be addressed by a voltage control 29 and provided with an individual voltage. Thus, from each well 6,6' one or more liquid drops may be displaced to the hydrophobic upper surface 16 of the flat polymer film 14 using the principle of electrowetting. Importantly, the displacement can be done for each well individually, so that reaction reagents 10 or liquids containing the biological sample 9 may be individually displaced at the time they are required on the film 14.

In FIG. 2A, the at least one well 6 for positioning a biological sample 9 is arranged towards the outer, lateral side 28 of the container 2. The at least one well 6 is additionally surrounded from an electrically conductive material 27. The electrically conductive surrounding 27 is in this variant extends to form the major part of the core of the container 2. In this way, major parts of the base side 4 of the container 2 are made of electrically conductive material 27, too. This allows processing a liquid droplet 19, which is positioned on the hydrophobic upper surface 16 of the film 14 and which contacts the base side 4 of the container 2, by electrowetting using the electrically conductive parts of the base side 4 of the container 2 as a ground electrode. Accordingly, in this variant, the guided movement of the liquid droplet 19 may be further stabilized.

When the container 2 itself is subjected to a heating step, for example to promote cell lysis within the at least one well 6 for positioning the biological sample and/or a reaction reagent, it is preferred that part of the container 2 is made from a thermally isolating material or that thermally insulating gaps are provided around the zone of higher temperature.

In a preferred embodiment, the container 2 comprises means for identification 30, which are selected from a group comprising a barcode and an RFID (radiofrequency identification) tag or another integrated chip. As such means for identification 30 are well known to the person skilled in the art, they should not be described in more detail here. Identification means 30 are especially preferred when the container 2 of the biological sample processing system 1 is used in an automated manner, while storing information for example about the biological sample positioned in a well 6 of the container 2. In addition, tracking of a particular sample is possible even in a large laboratory system.

When a solid substrate 24 comprising the biological sample 9 is positioned in the at least one well 6 of the container, this well 6 preferably comprises retention means 31 for preventing the solid substrate 24 to block the opening 8 of said well 6. The retention means 31 are selected from a group comprising a filter, a frit (see FIG. 1) and relief structures (see FIG. 2B). However, other retention means 31 well known in the art may be used for these purposes.

The FIGS. 2A and 2B each show a container 2 having an analyzing area 33. A container 2 having an analyzing area 33 is preferred, when certain areas of the hydrophobic upper surface 16 of the flat polymer film 14 should be accessible by optical means 38. In the simplest embodiment, a cut-out section defines the analyzing area 33, preferably in the outer lateral side 28 of the container 2. The respective region of the hydrophobic upper surface 16 of the film 14, underlying the cut-out, is in this way accessible for optical means 38. Such optical means are e.g. a human eye or an optical device. FIGS. 2A and 2B show exemplarily a preferred position of an optical means in relation to the analyzing area 33. Most preferably, the analyzing area 33 is positioned above that region of the hydrophobic upper surface 16, which is accomplished to the processing of a biological sample 9 using sequencing, especially preferred when as the sequencing method sequencing by hybridization method is performed. Preferably, optical devices 38 are selected from a group comprising a standard microscope, a camera system, a light guiding system such as fiber optics, a scanner, and adaptations or combinations thereof. For example, in a very simple embodiment, a camera, a simple CCD or a PMT (Photo Multiplier Tube) is used together with a light source, such as an LED, which serves as an excitation source for fluorescent tags on the film 14. If a light guiding system is used, the excitation- and/or measurement device may be located aside of the container 2. Thus, automatic sample processing and final analysis can be carried out on the same polymer film 16 and on the electrode array 21.

As shown in the FIGS. 2A and 2B, the container 2 preferably comprises a support rim 45 when having an analyzing area 33. This support rim 45 extends along the outer lateral side 28 of the container 2 while bordering the analyzing area 33. Accordingly, this support rim 45 may also comprise one or more protrusions 5 at its bottom side, which are attached to the hydrophobic upper surface 16 of the flat polymer film 14. This support rim 45 supports the container 2 having a cut-out when positioned on the film 14.

In a special user friendly variant, a multitude of containers 2 having at least one analyzing area 33 is arranged in such a way, that each analyzing area 33 is easily accessible by one optical device 38. One possible way would be an essentially circular arrangement of the containers 2 around a rotary optical device 38. Alternatively, the containers 2 can be stored in vertical or horizontal rows of adequate carrier, and the optical device 38 or the carrier with the row of container 2 are shifted manually or automatically into a position in which the analyzing 33 is accessible by the optical device 33.

Both, the container 2 and the flat polymer film 14 can be provided to the user either as separate components that remain to be assembled when the processing of a biological sample 9 is to be started. In an alternative embodiment however, these two components can be provided as a cartridge 40. In this case, the cartridge comprises both, container 2 and the flat polymer film 14, which are attached to one another for example by gluing or welding or other appropriate means to stably attach these two components.

Preferably, the container 2 or the cartridge 40 comprises a cover 43 for protecting the wells 6,6' and their content from outside influences. Such a cover 43 may be sealingly attached to the top side 7 of the container 2. The attachment may be reversible. In a preferred variant, the cover 43 is a thin film, which optionally is made of a pierceable material. In this way, the wells 6,6' of the container 2 may be preloaded. Safe storage is allowed by applying the film cover 43 onto the container 2. Only upon start of the sample processing, the film cover 43 is pierced open and the wells 6,6' of the container 2 are accessible for the user. Additionally, the container 2 or the cartridge 40 can be covered with a cover 43 as well.

In a second aspect, the present invention relates to a liquid droplet manipulation instrument 20. In a preferred embodiment, this liquid droplet manipulation instrument 20 is accomplished to be used in the biological sample processing system 1 according to the first aspect of the present invention. However, the liquid droplet manipulation instrument 20 may be used independently of the biological sample processing system 1.

The liquid droplet manipulation instrument 20 according to the second aspect of the present invention comprises at least one array of electrodes 21 for inducing a movement of a liquid droplet by electrowetting. The liquid droplet manipulation instrument 20 also comprises a substrate 22 for supporting the electrode array 21, and a control unit 23. The control unit 23 comprises at least one electrode selector 34, which is connected with at least one voltage control 29. The electrode selector 34 is accomplished to individually select each electrode 35 of the electrode array 21. Furthermore, the electrode selector 34 is accomplished to provide the selected electrode 35 with a voltage which is controlled by the voltage control 29. At least the electrode selector 34 and the voltage control 29 are controlled by a central processing unit 36, which is comprised by the control unit 23. The central processing unit 36 is accomplished to control the electrode selector 34 and the voltage control 29 to individually select at least one electrode 35 and to provide the selected electrode 35 with an individual voltage pulse. Preferably, the individual voltage pulse is selected from a group comprising a ground voltage and a drive voltage. With the selection and provision of an individual voltage pulse, the selected electrode 35 is defined as a drive electrode 35' or as a ground electrode 35".

The electrodes 35 of the electrode array 21 may have various shapes. Generally, those shapes of electrodes 35 are preferred which are suitable to establish an array of these electrodes 35. The FIGS. 3A-3D show some examples of preferred electrode-shapes. As can be seen in FIG. 3A, the electrodes 35 may have a rectangular shape. Here, the electrodes 35 have a square shape; however, other rectangular shapes may as well be suitable. In FIG. 3B, the electrodes 35 are shown as having a hexagonal shape, in FIG. 3C as having a circular shape and in FIG. 3D as having a triangular shape. However, other shapes may be suitable as well, as long as the electrodes 35 are able to establish an array and are accessible by electrode contacting lines.

Preferably, the central processing unit 36 comprises activatable software 37. This software 27 enables the central processing unit 36 to control the electrode selector 34 and the voltage control 29 to individually select at least one electrode 35 and to provide the selected electrode 35 with an individual voltage pulse.

The control unit 23 preferably comprises a power supply 44. This power supply 44 provides at least the central processing unit 36 and the voltage control 29 with electric power. Depending on the embodiments of other elements, such as the electrode selector 34, the power supply 44 may additionally provide also other elements with electric power.

The control unit 23 is capable to define a path for a guided movement of a liquid droplet 19 by the selection of a series of subsequent drive electrodes 35'. Thereby at least one of these selected drive electrodes 35' is subsequently provided with a drive voltage pulse along said path, under the control of the control unit 23. Furthermore the control unit 23 is accomplished to essentially simultaneously provide at least one electrode 35", which is adjacent to the pulsed drive electrode 35' and different to the selected drive electrode 35' of the path, with a ground voltage pulse.

Such a path for a guided movement of the liquid droplet is each shown in the FIGS. 3A to 3D. The subsequent selected drive electrodes 35' are indicated. The actual drive electrode 35' is shown to be that electrode 35, upon which the liquid droplet 19 is positioned. The direction of the planned guided movement of the liquid droplet 19 is indicated with an arrow. In that direction, subsequent electrodes 35' along the path will be provided with a drive voltage pulse.

Preferably, the size, respectively the diameter of the liquid droplet 19 slightly exceeds the diameter of an electrode 35. Most preferably, for the guided movement by electrowetting, the liquid droplet touches not only the actual drive electrode 35' but slightly touches simultaneously the subsequent electrode 35' which will become the next actual drive electrode 35'. However, the adjustment of electrode size in relation to liquid droplet sizes is within the knowledge of the person skilled in the art and should not be repeated here. However, the actual size and design of the electrodes and the desired size of the liquid droplets 19 must be in accordance with each other and with the praxis of electrowetting.

According the second inventive aspect, the presence of at least one ground electrode 35" adjacent to the liquid droplet 19 to be moved provides a stabilizing effect to its movement. The FIGS. 3A-3D indicate those electrodes 35" that might be provided with a ground voltage pulse. Those ground electrodes 35" are preferably adjacent to the pulsed drive electrodes 35' and different or identical to the selected drive electrodes 35' of the path. The provision with the ground voltage pulse is preferably carried out essentially simultaneously to the provision with the drive voltage pulse. Alternatively, the provision with the ground voltage pulse is to be carried out simultaneously to the provision with the drive voltage pulse.

According to a preferred variant of the liquid droplet manipulation instrument 20, the control unit 20 is accomplished to provide at least two electrodes 35" which are adjacent to the pulsed drive electrode 35' and different to the selected drive electrode 35' of the path with a ground voltage pulse. Preferably, these at least two selected ground electrodes 35" are subsequent electrodes 35 on the same side of the path.

As shown in the FIGS. 3A-3B, ground electrodes 35" may be selected from electrodes 35 along the path, adjacent to the path and adjacent to the liquid droplet 19. Preferably, the selected ground electrodes 35" are on the same side of the path. When a group of three or more electrodes 35" is to be provided with a ground voltage potential essentially simultaneously, at least two first electrodes 35" are preferably selected from one side of the path. The remaining electrodes 35" of that group may however be selected from that side of the path being opposite to the first two ground electrodes 35" of that group. However, even when a group of ground electrodes 35" are selected from two sides of the path, they are provided with the ground voltage pulse essentially simultaneously or simultaneously to the pulsed drive electrode 35'. If a group of electrodes 35" is simultaneously provided with a ground voltage pulse, the other electrodes 35" may be adjacent to the path and ahead of the liquid droplet 19, adjacent to the path and behind the liquid droplet 19 or both.

In one variant of the liquid droplet manipulation instrument 20, a group of 2 or more electrodes 35 may be provided with a drive voltage pulse essentially simultaneously. In this case, a liquid droplet 19' of a larger volume may be moved. However in this variant it is preferred that essentially simultaneously or simultaneously a group of 2 or more electrodes 35 are provided with a ground voltage pulse to sufficiently support the liquid droplet 19' with the larger volume.

In a preferred variant of the liquid droplet manipulation instrument 20, the control unit is accomplished to provide at least one selected electrode with a stop voltage pulse for generating a stop electrode 35'". Preferably, the provided stop voltage pulse is different to the drive voltage pulse and the ground voltage pulse.

The voltage pulses for defining a selected electrode 35 as a drive electrode preferably are between 20 and 100 V. The voltage pulses for defining a selected electrode 35 as a stop electrode preferably are between −50 V and +50 V. As shown in the FIGS. 3A-3D, selected stop electrodes 35'" are adjacent to the path, different to the selected drive electrode 35' of the path and different to the at least one selected ground electrode 35" adjacent to the path. Furthermore, stop electrodes 35'" are selected from such electrodes 35 adjacent to the path, where the path provides a change of direction for the liquid droplet 19 movement. A stop electrode 35'" supports the direction change of the liquid droplet movement along the path.

The FIGS. 3A-3D show exemplarily possible positions of stop electrodes 35'" along the path. Preferably, at least one electrode 35'" along the path at a place of direction change is provided with a stop voltage pulse. However, more than one electrode 35''' in that area may be selected to be provided with a stop voltage pulse, as shown in FIG. 3D. Here, two ore more electrodes are selected as stop electrode 35''' at the point of direction change to support the liquid droplet movement.

The FIGS. 3B and 3C show exemplary a virtual grid of the electrode array 21. Each grid point 39 of the virtual grid is established by the geometrical centre of each electrode 35 of the electrode array 21. FIG. 3B shows a hexagonal grid according to the hexagonal shape and dense packing of each electrode 35 of the electrode array 21. FIG. 3C shows an orthogonal grid based on the orthogonal arrangement of electrode 35, this time exhibiting essentially circular shape. Preferably, subsequent electrodes for defining the path, subsequent selected ground electrodes 35'', and/or subsequent selected stop electrodes 35''' are defined by the closest distance between two grid points 39 of that virtual grid. In this way a continuous liquid droplet movement may be ensured. The hexagonal arrangement of the electrodes array 21 is preferred over the orthogonal arrangement because of the higher degree of freedom.

FIG. 1 shows exemplarily the position of the electrodes 35 in relation to the substrate 22. Preferably, the electrodes 35 of the electrode array 21 are positioned in relation to the substrate 22, so that the upper surface of the electrodes 35 are aligned substantially flush with the upper surface of the substrate 22. Alternatively, the electrodes 35 of the electrode array are positioned within the substrate 22 and enclosed by it (see left hand side on FIG. 1). It is preferred to position the electrodes 35 as close to the liquid droplets 19 as possible in order to be able to reduce the voltage necessary for electrowetting. Thus, electrodes 35 flush with the upper surface of the substrate 22 and very thin polymer films are particularly preferred. As a material for the thin polymer films, e.g. food wraps, and stretchable wax films can be used.

In a preferred embodiment, the liquid droplet manipulation instrument 20 according to the present invention is accomplished to accommodate a container 2 for large volume processing and to simultaneously accommodate a flat polymer film 14 with a hydrophobic upper surface 16. In case a container 2 for large volume processing and a flat polymer film 14 comprising a hydrophobic upper surface 16 are attached to the liquid droplet manipulation instrument 20, a system is formed suited for biological sample processing of a sample 9 positioned within the container 2. Such a system preferably corresponds to the biological sample processing system 1 according to the first aspect of the present invention.

In another variant, the liquid droplet manipulation instrument 20 according to the present invention is accomplished to accommodate a cartridge 40. Said cartridge comprises a container 2 and a flat polymer film 14 as previously described herein. Container 2 and film 14 of the cartridge 40 are attached to one another by gluing or welding, or by other appropriate means to stably connect the container 2 and the film 14. In case such a cartridge 40 is attached to this variant of the liquid droplet manipulation instrument 20, a biological sample processing system 1 according to the first aspect of the present invention may be formed.

In one variant, the liquid droplet manipulation instrument 20 comprises at least two ore more electrode arrays 21. Preferably, the electrode arrays 21 are arranged essentially horizontal within the liquid droplet manipulation system 20. In this variant, the instrument 20 is accomplished to accommodate at least two or more containers 2 together with two or more flat polymer films 14, or to accommodate at least two or more cartridges 40. Preferably, the container 2 and the film 14 or the cartridge 40 may be positioned essentially above the electrode array. However, it is also possible to position these components essentially sideways or laterally, when the electrode arrays are not aligned essentially horizontally but essentially vertical.

In an especially preferred embodiment, the biological sample processing system 1 according to the first aspect of the present invention comprises a liquid droplet manipulation instrument 20 according to the second aspect of the present invention and as discussed in detail above. The embodiment of the liquid droplet manipulation instrument 20 as well as the embodiment of the biological sample processing system 1 may be chosen by selecting the various features discussed above, depending on the question addressed. If not stated otherwise, the various features presented within this application may all be combined with each other.

In FIG. 1, a biological sample processing system 1 comprising a liquid droplet manipulation instrument 20 is shown. The liquid droplet manipulation instrument 20 comprises a reception element 46 to safely receive the container 2 and the film 14.

In the embodiment shown, the positioning elements 25 of the liquid droplet manipulation instrument 20 are comprised by the reception element 46.

FIG. 3A shows an electrode array 21 according to such an especially preferred embodiment of a biological sample processing system 1. This Figure shows an enlarged top view of a distinct section of FIG. 1, indicated as a rectangle with a dotted line. The position of the at least one well 6 for positioning a biological sample 9 in relation to the defined path on the electrode array 21 is indicated by a dotted circular line in FIG. 3A. The opening 11 at the bottom of the at least one well 6, the passage of the channel 12 or the orifice 13 at the base side 4 of the container 2 respectively are indicated as an inner circle of a dotted line. A liquid 18 or a liquid droplet 19 is transferred from the well 6 through the channel 12 on the hydrophobic upper surface 16 of the flat polymer film 14, namely above the electrode array 21 of the liquid droplet manipulation instrument 20. A liquid portion 19' is indicated in the center of the electrode array 21 shown. This liquid portion 19' covers at least one selected drive electrode 35' from the electrode path. Preferably, the liquid portion covers at least partially subsequent electrodes 35' from the path. According to FIG. 3A, the liquid portion 19' covers additionally electrodes 35'' selected to be provided with a ground voltage pulse. A liquid droplet 19 is separated from the liquid portion 19' by the provision of a drive voltage pulse to an electrode 35' subsequent to the initial drive electrode 35' along the path. The liquid droplet 19 is then guided on along the path in a first direction, and after a direction change, in a second direction. At the position of the direction change, a stop electrode 35''' is generated to stabilize the direction change.

After e.g. a lysis step performed in a well 6 of the container and displacing a liquid portion 19,19', preferably comprising at least parts of the biological sample 9 of the well 6, further processing may be performed on the hydrophobic upper surface 16 of the flat polymer film 14. For processing a liquid droplet 19 with a DNA purification step, the use of magnetic beads is especially preferred. In this case, the liquid droplet manipulation instrument 20 of the biological sample processing system 1 comprises preferably at least one magnet 41. This magnet 41 controls the magnetic beads during the processing in the gap 17 on the upper hydrophobic side 16 of the flat polymer film 14. Suitable magnets may be electromagnets or permanent magnets. The magnet 41 is arranged preferably on that side of the substrate 22 of the instrument, which is not covered by an electrode array 21. The magnet 41 is alternatively arranged preferably on that side of the substrate 22 of the instrument 20, which is not abutted by the flat polymer film 14.

For processing a liquid droplet 19, which preferably comprises a biological sample 9, with a heat dependent processing step such as a PCR, the liquid droplet manipulation instrument 20 of the biological sample processing system 1 preferably comprises at least one heating element 42. This heating element 42 is preferably arranged on that side of the substrate 22 of the instrument 20, which is opposite to the side of the substrate 22 being abutted with the flat polymer film 14. The at least one heating element 42 is accomplished to provide at least one temperature zone with a predefined temperature on the upper hydrophobic surface 16 of the flat polymer film 14. If the liquid droplet manipulation device 20 comprises one heating element 42, PCR may be performed by keeping the liquid droplet 19 comprising a biological sample 9 within the single temperature zone, while changing the temperature within that single zone accordingly. If two heating elements 42 are used, a PCR may be done by moving the liquid droplet 19 comprising a biological sample 9 between the two zones, wherein the temperature of each zone is adopted according to the temperature required for the cycling steps. When processing a liquid droplet 19 comprising a biological sample 9 by PCR, the biological sample processing system 1 comprises in an especially preferred variant at least three heating elements 42 for providing at least three different temperature zones on the upper hydrophobic surface 16 of the flat polymer film 14. FIG. 1 shows a biological sample processing system 1 having three heating elements 42 underneath the support substrate 22 and opposite to the side being abutted with the flat polymer film 14. Each temperature zone has a predefined temperature to enable a PCR being performed on the upper hydrophobic surface 16 of the flat polymer film 14. Most preferably, one temperature zone comprises a temperature for denaturizing double stranded nucleic acid, one temperature zone comprises a temperature enabling the annealing of pre-selected primer, and one temperature zone comprises a temperature enabling a polymerase to elongate the annealed primer to the full strand. Additionally, the biological sample processing system 1 may comprise a fourth heating element 42 providing a temperature of about 4° C. Utilizing at least three heating elements 42 underneath the support substrate 22 has the advantage that the selected temperatures can be kept constantly over the entire reaction time and the droplets can be moved from one temperature region to another. This movement allows for rapid temperature changes within the droplets 19, which are much faster than achievable by changing the temperature of the heater element 42 while keeping the droplet 19 in place.

In a further variant of the biological sample processing system 1, a layer of low vapor pressure liquid connects the lower surface 15 of the flat polymer film 14 with the upper surface of the at least one electrode array 21 to reduce the formation of air bubbles in-between. Preferably, the low vapor pressure liquid is silicon oil; however, other low vapor pressure liquids may be used as well.

FIG. 4 shows top views of a grid-like electrode array 21 according to a first preferred embodiment and similar to the array of FIG. 3A with rectangular electrodes 35. In this partial and schematic presentation, a particularly preferred liquid droplet manipulation instrument 20 is shown, the liquid droplet manipulation instrument 20 comprising:

(a) at least one electrode array 21 for inducing a movement of a liquid droplet 19 by electrowetting;
(b) a substrate 22 supporting the at least one electrode array 21; and
(c) a control unit 23 comprising at least one electrode selector 34 connected with at least one voltage control 29, the at least one electrode selector 34 being accomplished to individually select each electrode 35 of the at least one electrode array 21 and to provide the selected electrode 35 with a voltage controlled by the voltage control 29; the control unit 23 further comprising a central processing unit 36 for controlling the electrode selector 34 and the voltage control 29 to individually select at least one electrode 35 and to provide the at least one selected electrode 35 with an individual voltage pulse which is selected from a group comprising a drive voltage, a ground voltage, and a stop voltage, thus defining the selected electrode 35 as a drive electrode 35', a ground electrode 35", or a stop electrode 35'''.

According to the present invention the control unit 23 of the liquid droplet manipulation instrument 20:

(d) is capable to define a path for a guided movement of at least one of a liquid droplet 19 and a liquid portion 19' of a larger volume that covers more than one electrode 35' of one electrode array 21 by the essentially simultaneous selection of a group of two or more subsequent drive electrodes 35' of said electrode array 21, and to provide each one of these selected drive electrodes 35' with a drive voltage pulse along said path; and
(e) is accomplished to essentially simultaneously provide a group of two or more electrodes 35 adjacent to or identical with the pulsed drive electrodes 35' with a ground or stop voltage pulse.

Figure 4A:
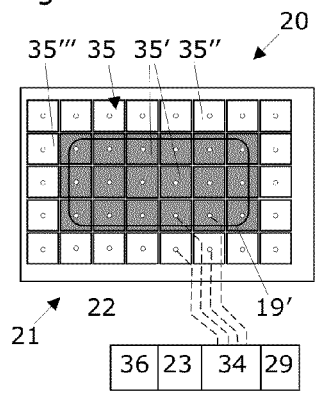
FIG. 4A a liquid portion of a larger volume covers about 18 pulsed drive electrodes of the same electrode array.

FIG. 4A shows a liquid portion 19' of a larger volume that covers about 18 pulsed drive electrodes 35' of the same electrode array 21. Preferably these 18 electrodes 35 have been activated for collecting this liquid portion 19' of a larger volume, the activated electrodes 35' attracting the liquid or at least keeping it in a stable volume. Most preferably, this liquid portion 19' of a larger volume is kept on the hydrophobic upper surface 16 of a flat polymer film 14 and within a gap 17, the flat polymer film 14 being exposed to the substrate 22 with the at least one electrode array 21 (compare with FIG. 1). Situated around the activated electrodes 35' (shown in grey), more electrodes 35 are defined as ground electrodes 35" or stop electrodes 35''' (shown in white). All electrodes 35 are operatively connected to the electrode selector 34 of the control unit 23 (only partially shown in FIG. 4A and present but not shown in the FIGS. 4B and 4D).

Figure 4B:
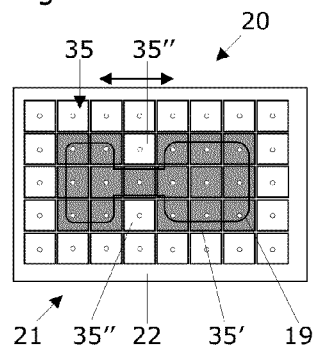
FIG. 4B a group of two electrodes identical with previously pulsed drive electrodes are provided with a ground voltage pulse.

FIG. 4B shows a group of two electrodes 35" that are identical with previously pulsed drive electrodes 35' that now are provided with a ground voltage pulse. This causes the liquid portion 19' of a larger volume to draw back to the activated electrodes 35' and induces a partial separation (see double arrow) of the liquid portion 19' of a larger volume into two smaller portions 19' that still cover at least two pulsed drive electrodes 35' of the same electrode array 21.

Figure 4C:
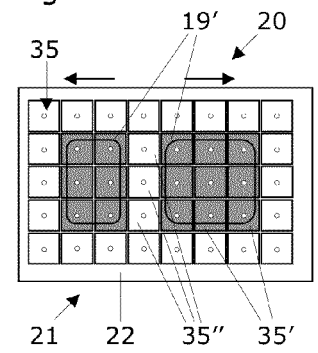
FIG. 4C a group of three electrodes identical with previously pulsed drive electrodes are provided with a ground voltage pulse.

FIG. 4C shows a group of three electrodes 35" that are identical with previously pulsed drive electrodes 35' and that now are provided with a ground or stop voltage pulse (the latter even enhancing the separation effect). This causes the liquid portion 19' of a larger volume to now completely separate (see one-sided arrows to the left and right) into two smaller portions 19' that still cover at least two pulsed drive electrodes 35' of the same electrode array 21.

Similar than using a drive path of three rows of electrodes 35 (as shown in FIG. 4), separation of a small volume, i.e. a single liquid droplet 19 can also be performed when using the same particularly preferred liquid droplet manipulation instrument 20 (see FIG. 5).

FIG. 5 shows top views of a grid-like electrode array according to a second preferred embodiment and similar to the array of FIG. 3A with rectangular electrodes.

Figure 5A:
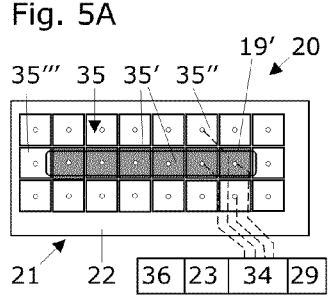
FIG. 5A a liquid portion of a larger volume covers about 6 pulsed drive electrodes of the same electrode array.

In FIG. 5A, a liquid portion 19' of a larger volume covers about 6 pulsed drive electrodes 35' of the same electrode array 21. Around the activated electrodes 35' (shown in grey), more electrodes 35 are defined as ground electrodes 35" or stop electrodes 35'" (shown in white). All electrodes 35 are operatively connected to the electrode selector 34 of the control unit 23 (only partially shown in FIG. 5A and present but not shown in the FIGS. 5B and 5D).

Figure 5B:
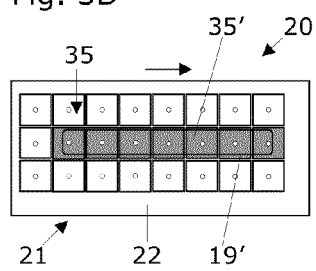
FIG. 5B an additional drive electrode of the same electrode array is activated so that the liquid portion now covers about 7 drive electrodes.
Figure 5C:
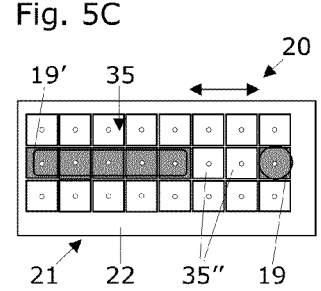
FIG. 5C opposite to the direction, where the additional drive electrode was activated in FIG. 5B, another drive electrode is activated and a group of two electrodes identical with previously pulsed drive electrodes are provided with a ground voltage pulse.

In order to separate or dispense a liquid droplet 19 from the remaining liquid portion 19' of a larger volume, an additional drive electrode 35' of the same electrode array 21 is activated so that the liquid portion 19' now covers about 7 drive electrodes 35' (see FIG. 5B, on-sided arrow to the right). Then, opposite to the direction, where the additional drive electrode 35' was activated in FIG. 5B, another drive electrode 35' is activated and a group of two electrodes 35" identical with previously pulsed drive electrodes 35' are provided with a ground or stop voltage pulse. This causes a liquid droplet 19 to be dispensed and the remaining liquid portion 19' of a larger volume to move in different directions (see double arrow in FIG. 5C). Providing the group of two electrodes 35" with a stop pulse even enhances the desired separation effect.

A combination of using a drive path of three rows of electrodes 35 (as e.g. shown in FIG. 4) and an electrode path of a single electrode row that closely reaches to the electrode array 21 (compare with FIG. 3A) is preferably used for dispensing small liquid volumes, i.e. single liquid droplets 19 when utilizing the same particularly preferred liquid droplet manipulation instrument 20 (see FIG. 6).

FIG. 6 shows top views of a grid-like electrode array 21 according to a third preferred embodiment and similar to the array of FIG. 3A with rectangular electrodes 35 and an electrode path adjacent to the electrode array 21.

Figure 6A:
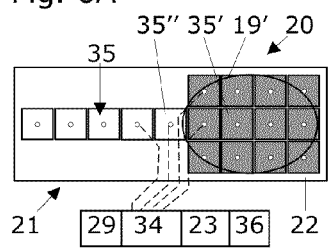
FIG. 6A a liquid portion of a larger volume covers about 10 activated electrodes of the electrode array.

In FIG. 6A, a liquid portion 19' of a larger volume covers about 10 activated electrodes 35' of the electrode array 21. All electrodes 35 of the electrode path are inactive (e.g. on a ground or on a stop potential). Preferably these 12 electrodes 35 have been activated for collecting this liquid portion 19' of a larger volume, the activated electrodes 35' attracting the liquid or at least keeping it in a stable volume. Most preferably, this liquid portion 19' of a larger volume is kept on the hydrophobic upper surface 16 of a flat polymer film 14 and within a gap 17, the flat polymer film 14 being exposed to the substrate 22 with the at least one electrode array 21 (compare with FIG. 1). Deactivating the electrodes of the electrode array 21 would not substantially change the position and shape of the liquid portion 19' of a larger volume. All electrodes 35 are operatively connected to the electrode selector 34 of the control unit 23 (only partially shown in FIG. 6A and present but not shown in the FIGS. 6B to 6F).

Figure 6B:
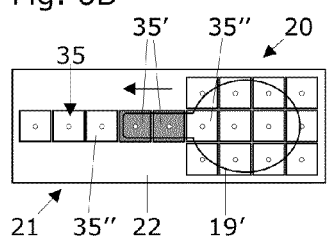
FIG. 6B the first two adjacent drive electrodes of the electrode path are activated and the previously activated 12 electrodes are inactivated.
Figure 6C:
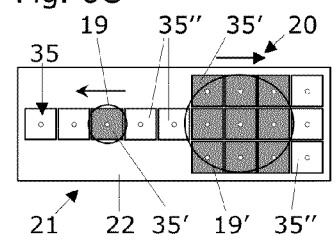
FIG. 6C the third drive electrode of the electrode path is activated, the first two adjacent drive electrodes are inactivated and a group of 9 electrodes of the electrode array are activated, the remaining liquid portion now covering about 9 electrodes of the electrode array.

In order to separate or dispense a liquid droplet 19 from the remaining liquid portion 19' of a larger volume, the first two adjacent drive electrodes 35' of the electrode path are activated and the previously activated 12 electrodes 35 of the array 21 are inactivated (see FIG. 6B). Inactivation in this case means providing the 12 electrodes 35 of the electrode array 21 with a ground voltage pulse. This combined action of the first two adjacent drive electrodes 35' of the electrode path and the 12 electrodes 35 of the array 21 causes the liquid portion 19' of a larger volume to move to the left and spread over the first two adjacent drive electrodes 35' of the electrode path (see one-sided arrow to the left).

Consecutively (see FIG. 6C), the third drive electrode 35' of the electrode path is activated, the first two adjacent drive electrodes 35" are inactivated and a group of 9 electrodes 35' of the electrode array are activated as well. The same time, three electrodes 35" of the electrode array are inactivated. Inactivation in this case means providing the first two adjacent drive electrodes 35" of the path with a ground or with a stop pulse. This causes separation (or dispense) of a first liquid droplet 19 from the liquid portion 19' of a larger volume by moving the liquid droplet 19 to the third electrode 35 of the path and by moving back the residual liquid portion 19' to the activated electrodes 35' of the electrode array 21 (see one-sided arrows to the right and left). Providing the two adjacent drive electrodes 35" with a stop pulse even enhances the desired separation effect. The remaining liquid portion 19' now covers about 9 electrodes of the electrode array.

Then (see FIG. 6D), the fourth drive electrode 35' of the electrode path is activated, the second and third drive electrodes 35" are inactivated. Inactivation in this case means providing the second and third drive electrodes 35" of the path with a ground or with a stop pulse. This causes moving of the first liquid droplet 19 to the fourth electrode 35' of the path (see one-sided arrow to the left). The same time, the first drive electrode 35' of the electrode path is activated together with adjacent 9 electrodes 35' of the electrode array 21 and three electrodes 35" of the electrode array are kept inactivated. This causes the liquid portion 19' of a larger volume to move to the left and spread over the first adjacent drive electrode 35' of the electrode path (see one-sided arrow to the left). Inactivation with respect to the three electrodes 35" of the electrode array 21 forces a concentration of the residual liquid portion 19' of a larger volume to the electrodes 35' in vicinity to the electrode path.

In the following (see FIG. 6E), the fifth drive electrode of the electrode path is activated and the fourth drive electrode is inactivated. This causes moving of the first liquid droplet 19 to the fifth electrode 35' of the path (see one-sided arrow to the left). The same time, the first three drive electrodes 35' of the electrode path are activated and all electrodes of the electrode array are inactivated. This causes the liquid portion 19' of a larger volume to move to the left and spread over the first three drive electrode 35' of the electrode path (see one-sided arrow to the left).

Figure 6D:
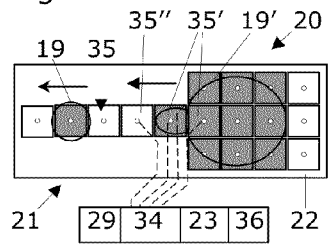
FIG. 6D the fourth drive electrode of the electrode path is activated, the second and third drive electrodes are inactivated, and the first drive electrode of the electrode path is activated together with adjacent 9 electrodes of the electrode array, three electrodes of the electrode array are inactivated.
Figure 6E:
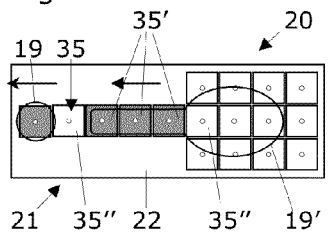
FIG. 6E the fifth drive electrode of the electrode path is activated, the fourth drive electrode is inactivated, and the first three drive electrodes of the electrode path are activated, all electrodes of the electrode array are inactivated.
Figure 6F:
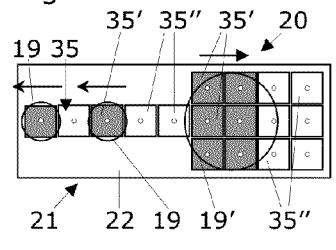
FIG. 6F the fifth drive electrode of the electrode path is activated and the fourth drive electrode is inactivated, the third drive electrode of the electrode path is activated together with 6 electrodes of the array and the first two drive electrodes of the electrode path are inactivated together with 6 electrodes of the array, the remaining liquid portion now covering about 8 electrodes of the electrode array.

Thereafter (see FIG. 6F), the fifth and third drive electrodes 35' of the electrode path stay activated while the fourth and the first two drive electrodes are inactivated. This causes keeping the first liquid droplet 19 on the fifth electrode 35' and separation of a second liquid droplet 19 on the third electrode 35' of the path (see one-sided arrows to the left). The same time, 6 electrodes 35 of the array 21 are activated, which causes the remaining liquid portion 19' withdrawing to the electrode array 21, from which it now covers about 8 electrodes (see one-sided arrow to the right). Before dispensing of a further (third) liquid droplet 19, the already separated liquid droplets 19 have at least to be moved to the next drive electrode 35' in each case and a similar situation is created as depicted in FIG. 6D.

In particular with respect to the FIGS. 4, 5, and 6, it is expressly noted that preferably, a dielectric layer is provided on the surface of the electrode array 21. Preferably, the dielectric layer is part of the substrate 22 of the liquid droplet manipulation instrument 20 or part of the flat polymer film 14. Deviating from the embodiment shown in FIG. 3A, the gap preferably 17 is closed on its upper side by a dielectric layer with a hydrophobic surface, so that the liquid droplets 19 or the liquid portions 19' are moved and manipulated in the gap 17 between two hydrophobic surfaces. The gap 17 may be partially or totally filled with a fluid that is not miscible with the liquid droplets 19 or the liquid portions 19', the fluid preferably being selected from air, a chemically inert gas (like e.g. N₂), and a non-aqueous liquid (like e.g. silicon oil or hexadecane). The substrate 22 may be selected from materials like a printed circuit board (PCB), a polymer, glass, or compound materials. Preferably, all electrodes 35 are arranged in the same plane; however arranging the electrodes 35 in different planes or in planes of different inclination is envisaged too.

In the context of the present application, "dispensing" liquid droplets 19 from larger portions 19', "splitting" liquid droplets 19 into smaller droplets, and "separating" larger portions 19' into several parts is termed manipulating liquid droplets 19 or liquid portions 19', whether the larger liquid portions 19' need "pumping" or not. In the context of the present application, "joining" small liquid droplets 19 with each other (e.g. for mixing reaction partners) or with larger liquid portions 19', and "assembling" larger liquid portions 19' is also termed manipulating liquid droplets 19 or liquid portions 19'. In the context of the present application, the controlled reduction of the size of an electrode array 21 with the goal of forcing a larger liquid portion 19' in a desired direction, e.g. to the site where an electrode part is joining the electrode array 21, is termed "pumping". In the context of the present application, a number or "grid" of equally sized electrodes 35 may be termed a "reservoir" or a "manipulation array". Any combination of features of the different embodiments of electrode arrays disclosed in this patent application that lays within the borders of the appended claims and that appears reasonable to a person of skill is comprised by the gist and scope of the present invention.

Similar reference numbers refer to similar parts, if they are not particularly discussed in detail.

List of reference numbers:

| | |
|---|---|
| 1 | biological sample processing system |
| 2 | container |
| 3 | top side of the container |
| 4 | base side of the container |
| 5 | protrusions of the container |
| 6, 6' | well of the container |
| 7 | top side of the well |
| 8 | opening at the bottom side of the well |
| 9 | biological sample |
| 10 | reaction reagent |
| 11 | opening of the well |
| 12 | channel of the container |
| 13 | orifice of the container |
| 14 | flat polymer film |
| 15 | lower surface of the flat polymer film |
| 16 | hydrophobic upper surface of the flat polymer film |
| 17 | gap |
| 18 | liquid |
| 19 | liquid droplet |
| 19' | liquid portion of a larger volume |
| 20 | liquid droplet manipulation instrument |
| 21 | electrode array |
| 22 | substrate of the instrument |
| 23 | control unit |
| 24 | solid substrate comprising the biological sample |
| 25 | positioning element |
| 26 | electrically insulating material |
| 27 | electrically conductive material |
| 28 | outer lateral side of container |
| 29 | voltage control |
| 30 | means for identification |
| 31 | retention means |
| 32 | system liquid |
| 33 | analyzing area |
| 34 | electrode selector |
| 35 | electrodes |
| 35' | drive electrode |
| 35" | ground electrode |

-continued

List of reference numbers:

| | |
|---|---|
| 35''' | stop electrode |
| 36 | central processing unit |
| 37 | software |
| 38 | optical means |
| 39 | grid point |
| 40 | cartridge |
| 41 | magnet |
| 42 | heating element |
| 43 | cover |
| 44 | power supply |
| 45 | support rim |
| 46 | reception element |
| 47 | nozzle |
| d | distance between the upper surface of the film and the base side of the container |

What is claimed is:

1. A liquid droplet manipulation instrument (20), comprising:
   (a) at least one electrode array (21) for inducing a movement of a liquid droplet (19) by electrowetting;
   (b) a substrate (22) supporting the at least one electrode array (21); and
   (c) a control unit (23) comprising at least one electrode selector (34) connected with at least one voltage control (29), the at least one electrode selector (34) being accomplished to individually select each electrode (35) of the at least one electrode array (21) and to provide the selected electrode (35) with a voltage controlled by the voltage control (29); the control unit (23) further comprising a central processing unit (36) for controlling the electrode selector (34) and the voltage control (29) to individually select at least one electrode (35) and to provide the at least one selected electrode (35) with an individual voltage pulse which is selected from a group comprising a drive voltage, a ground voltage, and a stop voltage, thus defining the selected electrode (35) as a drive electrode (35'), a ground electrode (35"), or a stop electrode (35'''); wherein
   (d) the control unit (23) is capable to define a path for a guided movement of at least one of a liquid droplet (19) and a liquid portion (19') of a larger volume that covers more than one electrode (35') of one electrode array (21) by the essentially simultaneous selection of a group of two or more subsequent drive electrodes (35') of said electrode array (21), and to provide each one of these selected drive electrodes (35') with a drive voltage pulse along said path; and
   (e) the control unit (23) is accomplished to essentially simultaneously provide a group of two or more electrodes (35) adjacent to or identical with the pulsed drive electrodes (35') with a ground or stop voltage pulse.

2. The liquid droplet manipulation instrument (20) of claim 1, wherein the electrodes (35) of said electrode array (21) are arranged in an orthogonal grid.

3. The liquid droplet manipulation instrument (20) of claim 1, wherein the electrodes (35) of said electrode array (21) exhibit an essentially square or circular shape.

4. The liquid droplet manipulation instrument (20) of claim 1, wherein the electrodes (35) of said electrode array (21) exhibit an essentially hexagonal or triangular shape.

5. The liquid droplet manipulation instrument (20) of claim 1, wherein the electrodes (35) of the at least one electrode array (21) are positioned in relation to the substrate (22), so that the upper surface of the electrode (35) is aligned substantially flush with the upper surface of the substrate (22), and/or the electrodes (35) of the electrode array are positioned within and enclosed by the substrate (22).

6. The liquid droplet manipulation instrument (20) of claim 1, being accomplished to accommodate at least one container (2) for large volume processing and at least one flat polymer film (14) with a hydrophobic upper surface (16).

7. The liquid droplet manipulation instrument (20) of claim 6, comprising at least one heating element (42) for providing at least one temperature zone with a predefined temperature on the hydrophobic upper surface (16) of the flat polymer film (14).

8. The liquid droplet manipulation instrument (20) of claim 1, being accomplished to accommodate at least one cartridge (40) comprising a container (2) and a flat polymer film (14) with a hydrophobic upper surface (16).

9. The liquid droplet manipulation instrument (20) of claim 8, comprising at least one heating element (42) for providing at least one temperature zone with a predefined temperature on the hydrophobic upper surface (16) of the flat polymer film (14).

10. A biological sample processing system (1) comprising a liquid droplet manipulation instrument (20) according to claim 1, the biological sample processing system (1) further comprising:
    (a) a container (2) for large volume processing having a top side (3) and a base side (4) and comprising at least one well (6) open at the top side (3) for positioning a biological sample (9) and/or a reaction reagent (10) therein, wherein the at least one well (6) comprises a bottom side (8) having at least one opening (11), the container (2) further comprising a channel (12) connecting the opening of the well (11) with an orifice (13) on the base side (4) of the container (2), and wherein the base side (4) of the container (2) comprises protrusions (5) distributed thereon; and
    (b) a flat polymer film (14) having a lower surface (15) and a hydrophobic upper surface (16), which is kept at a distance d to the base side (4) of the container (2) by the protrusions (5), the distance d defining at least one gap (17) when the container (2) is positioned on the flat polymer film (14), abutting the latter with its protrusions (5),
    wherein the container (2) and the flat polymer film (14) are reversibly attachable to the liquid droplet manipulation instrument (20).

11. The biological sample processing system (1) of claim 10, wherein the flat polymer film (14) is accomplished as an electrically insulating flat polymer film.

12. The biological sample processing system (1) of claim 10,
    wherein when the container (2) and the flat polymer film (14) are reversibly attached to the liquid droplet manipulation instrument (20), the lower surface (15) of the flat polymer film (14) abuts the at least one electrode array (21), the system (1) enabling displacement of at least one liquid droplet (19) from the at least one well (6) through the channel (12) of the container (2) onto the hydrophobic upper surface (16) of the flat polymer film (14) and above the at least one electrode array (21),
    and wherein the liquid droplet manipulation instrument (20) is accomplished to control a guided movement of said liquid droplet (19) on the hydrophobic upper surface (16) of the flat polymer film (14) by electrowetting and to process there the biological sample (9).

13. The biological sample processing system (1) or the cartridge (40) of claim 12, wherein the flat polymer film (14) is accomplished as an electrically insulating flat polymer film.

14. A method for processing a biological sample (9) with a biological sample processing system (1) of claim 12,
    wherein the container (2) and the flat polymer film (4) are reversibly attached to the liquid droplet manipulation instrument (20), so that the lower surface (15) of the flat polymer film (14) is abutting the at least one electrode array, and at least one liquid droplet (19) from the at least one well (6) is displaced through the channel (13) of the container (2) onto the hydrophobic upper surface (16) of the flat polymer film (14) and above the at least one electrode array (21), and
    wherein the liquid droplet (19) is processed by a guided movement on the hydrophobic upper surface (16) of the flat polymer film (14) by electrowetting controlled by the liquid droplet manipulation instrument (20).

15. The method of claim 14, wherein the container (2) and the flat polymer film (14) are provided as a cartridge (40) that comprises both, the container (2) and the flat polymer film (14), which are attached to one another by gluing or welding.

16. The method of claim 14, wherein the container (2) and the flat polymer film (14) are provided as separate components that remain to be assembled when the processing of a biological sample (9) is to be started.

17. The method of claim 14, wherein for separating a liquid droplet (19) from said liquid portion (19') of a larger volume, the control unit (23):
    (i) provides a drive voltage pulse to an initial drive electrode (35') and to an electrode (35') subsequent to the initial drive electrode (35') along said electrode path and thus moves the liquid droplet (19) in a first direction; and
    (ii) provides a drive voltage pulse to said group of two or more drive electrodes (35') of the electrode array (21) in order to move said liquid portion (19') of a larger volume in a second direction inverse to the first direction.

18. A method for processing a biological sample (9) with a biological sample processing system (1) of claim 10,
    wherein the container (2) and the flat polymer film (4) are reversibly attached to the liquid droplet manipulation instrument (20), so that the lower surface (15) of the flat polymer film (14) is abutting the at least one electrode array, and at least one liquid droplet (19) from the at least one well (6) is displaced through the channel (13) of the container (2) onto the hydrophobic upper surface (16) of the flat polymer film (14) and above the at least one electrode array (21), and
    wherein the liquid droplet (19) is processed by a guided movement on the hydrophobic upper surface (16) of the flat polymer film (14) by electrowetting controlled by the liquid droplet manipulation instrument (20).

19. The method of claim 18, wherein the container (2) and the flat polymer film (14) are provided as a cartridge (40) that comprises both, the container (2) and the flat polymer film (14), which are attached to one another by gluing or welding.

20. The method of claim 18, wherein the container (2) and the flat polymer film (14) are provided as separate components that remain to be assembled when the processing of a biological sample (9) is to be started.

21. The method of claim 18, wherein for separating a liquid droplet (19) from said liquid portion (19') of a larger volume, the control unit (23):
    (i) provides a drive voltage pulse to an initial drive electrode (35') and to an electrode (35') subsequent to the initial drive electrode (35') along said electrode path and thus moves the liquid droplet (19) in a first direction; and (ii) provides a drive voltage pulse to said group of two or more drive electrodes (35') of the electrode array (21) in order to move said liquid portion (19') of a larger volume in a second direction inverse to the first direction.

* * * * *